(12) United States Patent
Heavelyn et al.

(10) Patent No.: US 11,823,779 B2
(45) Date of Patent: *Nov. 21, 2023

(54) MEDICAL DEVICE DATA BACK-ASSOCIATION, SYSTEM, APPARATUSES, AND METHODS

(71) Applicants: BAXTER INTERNATIONAL INC., Deerfield, IL (US); BAXTER HEALTHCARE SA, Glattpark (CH)

(72) Inventors: Troy David Heavelyn, Grayslake, IL (US); Curt Matthew Allen, Medina, NY (US); Phillip Edwin Fisk, Lockport, NY (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 73 days.

This patent is subject to a terminal disclaimer.

(21) Appl. No.: 17/526,699

(22) Filed: Nov. 15, 2021

(65) Prior Publication Data
US 2022/0076795 A1    Mar. 10, 2022

Related U.S. Application Data

(62) Division of application No. 16/408,978, filed on May 10, 2019, now Pat. No. 11,177,026.

(60) Provisional application No. 62/670,441, filed on May 11, 2018.

(51) Int. Cl.
| | | |
|---|---|---|
| *G16H 10/60* | (2018.01) | |
| *G16H 20/17* | (2018.01) | |
| *G16H 40/60* | (2018.01) | |
| *G16H 80/00* | (2018.01) | |

(52) U.S. Cl.
CPC .............. *G16H 10/60* (2018.01); *G16H 20/17* (2018.01); *G16H 40/60* (2018.01); *A61M 2205/3576* (2013.01); *A61M 2205/6072* (2013.01); *G16H 80/00* (2018.01)

(58) Field of Classification Search
CPC ........ G16H 10/60; G16H 40/67; G16H 40/63; G16H 15/00; G16H 20/17; G16H 40/60; G16H 20/00
See application file for complete search history.

(56) References Cited

U.S. PATENT DOCUMENTS

2010/0169120 A1*   7/2010  Herbst ................... G16H 40/67
                                                     707/E17.014
2013/0046871 A1*   2/2013  Vik ......................... H04L 67/12
                                                     709/223

* cited by examiner

*Primary Examiner* — Joseph D Burgess
(74) *Attorney, Agent, or Firm* — K&L Gates LLP

(57) ABSTRACT

A medical device data back-association system, apparatuses, and methods are disclosed. In an example embodiment, a server receives first medical device data from a medical device including a device identifier and stores the first medical device data to an unassociated record in a database after determining that there is no association between the device identifier and any patient identifier or medication order identifier. While the medical device is administering the medication to a patient, the server receives an identifier message including at least two of the device identifier, the patient identifier, and the medication order identifier. The server creates an identifier association between a medical record of the patient and the medical device using the identifier message. The server uses the identifier association to store subsequent medical device data from the medical device to the medical record of the patient.

20 Claims, 10 Drawing Sheets

MEDICAL DEVICE DATA BACK-ASSOCIATION, SYSTEM, APPARATUSES, AND METHODS

PRIORITY CLAIM

This application claims priority to and the benefit as a divisional application of U.S. patent application Ser. No. 16/408,978, filed May 10, 2019, now U.S. Pat. No. 11,177, 026, which is a non-provisional application of U.S. Provisional Patent Application No. 62/670,441, filed May 11, 2018, the entire contents of which are hereby incorporated by reference and relied upon.

BACKGROUND

Medical documentation is a critical component of a healthcare system. A patient's treatment is often based on proper documentation of their health condition, past treatments, and ongoing treatments. In addition, a patient's health documentation permits different clinicians from different practice areas to view the medical history of a patient for making fully-informed decisions to improve the health outlook of a patient.

Currently, a patient's health documentation is stored in an electronic medical record ("EMR"). While there is no universal format, EMRs typically contains a patient's physical characteristics, measured physiological parameters, diagnostic test results, a summary of medical procedures performed, and clinician notes. Many EMRs also include data transmitted from a medical device that is providing a therapy to a patient. The data from a medical device can include infusion therapy data or renal failure therapy data. In some known instances, a clinician manually enters infusion or dialysis data into an EMR.

Some recent advances enable an EMR server to store data (directly to a patient's EMR) that is received from an infusion or dialysis device. However, this automatic storage requires that a clinician provide an association between the medical device, patient, and medication order (or medical record) prior to providing treatment. For example, to make an association, a clinician has to use an interface of a device to open a medication order from a patient's EMR. The clinician may then enter a patient identifier and/or medical device identifier into the medication order to create an association.

If an association is not made, the EMR server receives the data, but does not have association information indicating to where the medical data is to be stored. As a result, some EMR servers will discard the received data while other EMR servers store the data in a temporary database location. To make an association after a treatment has began, a clinician has to manually copy the received data from the temporary database storage location to the patient's EMR, which is generally a time-consuming and inefficient process. Further, the clinician has to manually create the association between the medical device and the patient so that newly received data is automatically stored to the patient's EMR.

SUMMARY

The present disclosure sets forth systems, apparatuses and methods for providing medical record documentation by associating medical device data with a patient's electronic medical record ("EMR") regardless of when a treatment has begun. In some examples, a medical device is configured to enable back-association by displaying or providing a code indicative of a device identifier. A patient identifier and/or medication identifier may also be scanned or entered. The scanned identifiers are transmitted to a server configured to manage patient medical records. The server matches, for example, a scanned patient identifier to a patient identifier in a medical record. After a match occurs, the server associates the medical device identifier with the medical record. The server uses the association for storing medical device data having the device identifier to the medical record of the patient.

Aspects of the subject matter described herein may be useful alone or in combination with one or more other aspect described herein. Without limiting the foregoing description, in a first aspect of the present disclosure, an electronic medical record system includes a database stored in a memory device, the database configured to store a medication order to an electronic medical record ("EMR") of a patient. The medication order includes a medication order identifier and a patient identifier of the patient. The EMR of the patient includes the patient identifier. The electronic medical record system also includes a server communicatively coupled to the database and a memory storing machine-readable code or instructions, that when executed by a processor of the server, cause the server to perform certain operations. The operations include receiving first medical device data from a medical device via a network, the first medical device data including a device identifier of the medical device. The operations also include determining, at a first time, there is no association between the device identifier and any patient identifier or medication order identifier and storing the first medical device data to an unassociated record in the database. The operations further include receiving, while the medical device is administering the medication to the patient, an identifier message including at least two of the device identifier, the patient identifier, and the medication order identifier, and creating an association between the EMR of the patient and the medical device by matching the patient identifier or the medication order identifier of the identifier message to the medication order identifier or the patient identifier of the medication order. Additionally, the operations include receiving, at a second time that is after the association between the EMR of the patient and the medical device, second medical device data from the medical device, the second medical device data including the device identifier. The operations moreover include storing the second medical device data to the EMR of the patient based on the created association between the EMR of the patient and the medical device.

In accordance with a second aspect of the present disclosure, which may be used in combination with any other aspect listed herein unless stated otherwise, the server is configured to create the association between the EMR of the patient and the medical device by at least one of storing the device identifier and at least one of the patient identifier or the medication order identifier to an entry of an association record, storing the device identifier to the EMR of the patient, or storing the device identifier to the medication order of the patient.

In accordance with a third aspect of the present disclosure, which may be used in combination with any other aspect listed herein unless stated otherwise, the server is configured to, after the association between the EMR of the patient and the medical device is created, store the first medical device data to the EMR of the patient.

In accordance with a fourth aspect of the present disclosure, which may be used in combination with any other aspect listed herein unless stated otherwise, the server is configured to, cause at least one of the unassociated record or the first medical device data to be deleted from the database.

In accordance with a fifth aspect of the present disclosure, which may be used in combination with any other aspect listed herein unless stated otherwise, the device identifier of the identifier message is determined by scanning while the medical device is administering the medication to the patient, via a bar code scanner, at least one of alpha-numeric characters, a barcode, or a quick-response ("QR") code.

In accordance with a sixth aspect of the present disclosure, which may be used in combination with any other aspect listed herein unless stated otherwise, the server is configured to receive the identifier message from the bar code scanner or a computer on wheels connected to the bar code scanner.

In accordance with a seventh aspect of the present disclosure, which may be used in combination with any other aspect listed herein unless stated otherwise, the electronic medical record system further includes a gateway communicatively coupled to the medical device and the server via the network. The gateway is configured to receive the medical device data from the medical device in an INTCOM or EXTCOM format, convert the medical device data into an HL7 format, and transmit the formatted medical device data to the server.

In accordance with an eighth aspect of the present disclosure, which may be used in combination with any other aspect listed herein unless stated otherwise, the unassociated record is indexed in the database by the device identifier.

In accordance with a ninth aspect of the present disclosure, which may be used in combination with any other aspect listed herein unless stated otherwise, the medical device includes at least one of an infusion pump or a renal failure therapy machine.

In accordance with a tenth aspect of the present disclosure, which may be used in combination with any other aspect listed herein unless stated otherwise, an electronic medical record method includes storing, via a processor, to an electronic medical record ("EMR") in a database, a medication order of a patient, the medication order including a medication order identifier and a patient identifier, receiving, in the processor, first medical device data from a medical device via a network, the first medical device data including a device identifier of the medical device, storing, via the processor, the first medical device data to an unassociated record in the database after determining that there is no association between the device identifier and any patient identifier or medication order identifier, receiving, in the processor while the medical device is administering the medication to the patient, an identifier message including at least two of the device identifier, the patient identifier, and the medication order identifier, creating, via the processor, an association between the EMR of the patient and the medical device using the identifier message, receiving, in the processor, after the association between the EMR of the patient and the medical device, second medical device data from the medical device, the second medical device data including the device identifier, and storing, via the processor, the second medical device data to the EMR of the patient based on the created association between the EMR of the patient and the medical device.

In accordance with an eleventh aspect of the present disclosure, which may be used in combination with any other aspect listed herein unless stated otherwise, the method further includes after the association between the EMR of the patient and the medical device is created, storing the first medical device data to the EMR of the patient.

In accordance with a twelfth aspect of the present disclosure, which may be used in combination with any other aspect listed herein unless stated otherwise, the method further includes while the medical device is administering the medication to the patient, receiving at an interface of the medical device, an operator input for displaying the device identifier, and causing, via the medical device, the device identifier to be displayed on a screen of the medical device.

In accordance with a thirteenth aspect of the present disclosure, which may be used in combination with any other aspect listed herein unless stated otherwise, the device identifier is displayed via at least one of alpha-numeric characters, a barcode, or a quick-response ("QR") code.

In accordance with a fourteenth aspect of the present disclosure, which may be used in combination with any other aspect listed herein unless stated otherwise, the method further includes receiving, in a bar code scanner, first information that is indicative of the device identifier from reading the device identifier displayed on the screen of the medical device, receiving, in a bar code scanner, second information that is indicative of the patient identifier from reading the patient identifier provided on a patient wrist band, creating, via a computer connected to the bar code scanner, the identifier message, and transmitting, via the computer, the identifier message to the processor via the network.

In accordance with a fifteenth aspect of the present disclosure, which may be used in combination with any other aspect listed herein unless stated otherwise, the method further includes receiving, in the processor, the medication order in at least one HL7 message from a pharmacy server, and storing, via the processor, the medication order to the EMR of the patient using the patient identifier for association between the EMR of the patient and the medication order.

In accordance with a sixteenth aspect of the present disclosure, which may be used in combination with any other aspect listed herein unless stated otherwise, the medication order includes at least one of a medication name, a volume to be infused, a medication concentration, or a medication delivery rate.

In accordance with a seventeenth aspect of the present disclosure, which may be used in combination with any other aspect listed herein unless stated otherwise, the device identifier in the identifier message is encrypted, further comprising decrypting, via the processor the device identifier using a stored key.

In accordance with an eighteenth aspect of the present disclosure, which may be used in combination with any other aspect listed herein unless stated otherwise, an electronic medical record memory stores machine-readable code or instructions, that when executed by a processor, cause the processor to receive, while an infusion pump is administering a medication to a patient, an identifier message including at least two of a device identifier of the infusion pump, a patient identifier of the patient, and a medication order identifier of a medication, create an association between an EMR of the patient located in a database and the infusion pump using the identifier message, receive after the association between the EMR of the patient and the infusion pump, infusion pump data from the infusion pump, the infusion pump data including the device identifier, and store the infusion pump device data to the EMR of the patient based on the created association between the EMR of the patient and the infusion pump.

In accordance with a nineteenth aspect of the present disclosure, which may be used in combination with any other aspect listed herein unless stated otherwise, the electronic medical record memory stores further machine-readable code or instructions, that when executed by the processor, cause the processor to receive first infusion pump device data before the association between the EMR of the patient and the infusion pump, and store the first medical device data to an unassociated record in the database after determining that there is no association between the device identifier and any patient identifier or medication order identifier.

In accordance with a twentieth aspect of the present disclosure, which may be used in combination with any other aspect listed herein unless stated otherwise, the electronic medical record memory stores further machine-readable code or instructions, that when executed by the processor, cause the processor to, after the association between the EMR of the patient and the medical device is created, store the first medical device data to the EMR of the patient.

In accordance with a twenty-first aspect of the present disclosure, any of the structure and functionality illustrated and described in connection with FIGS. 1 to 11 may be used in combination with any of the structure and functionality illustrated and described in connection with any of the other of FIGS. 1 to 11 and with any one or more of the preceding aspects.

In light of the aspects above and the disclosure herein, it is accordingly an advantage of the present disclosure to provide a system that enables medical device data to be stored to a patient's EMR regardless of when an association is made between a medical device and a patient.

It is another advantage of the present disclosure to provide a system that enables medical device data to be transferred to a patient's EMR after an association is made.

The advantages discussed herein may be found in one, or some, and perhaps not all of the embodiments disclosed herein. Additional features and advantages are described herein, and will be apparent from, the following Detailed Description and the figures.

DETAILED DESCRIPTION

Figure 1:
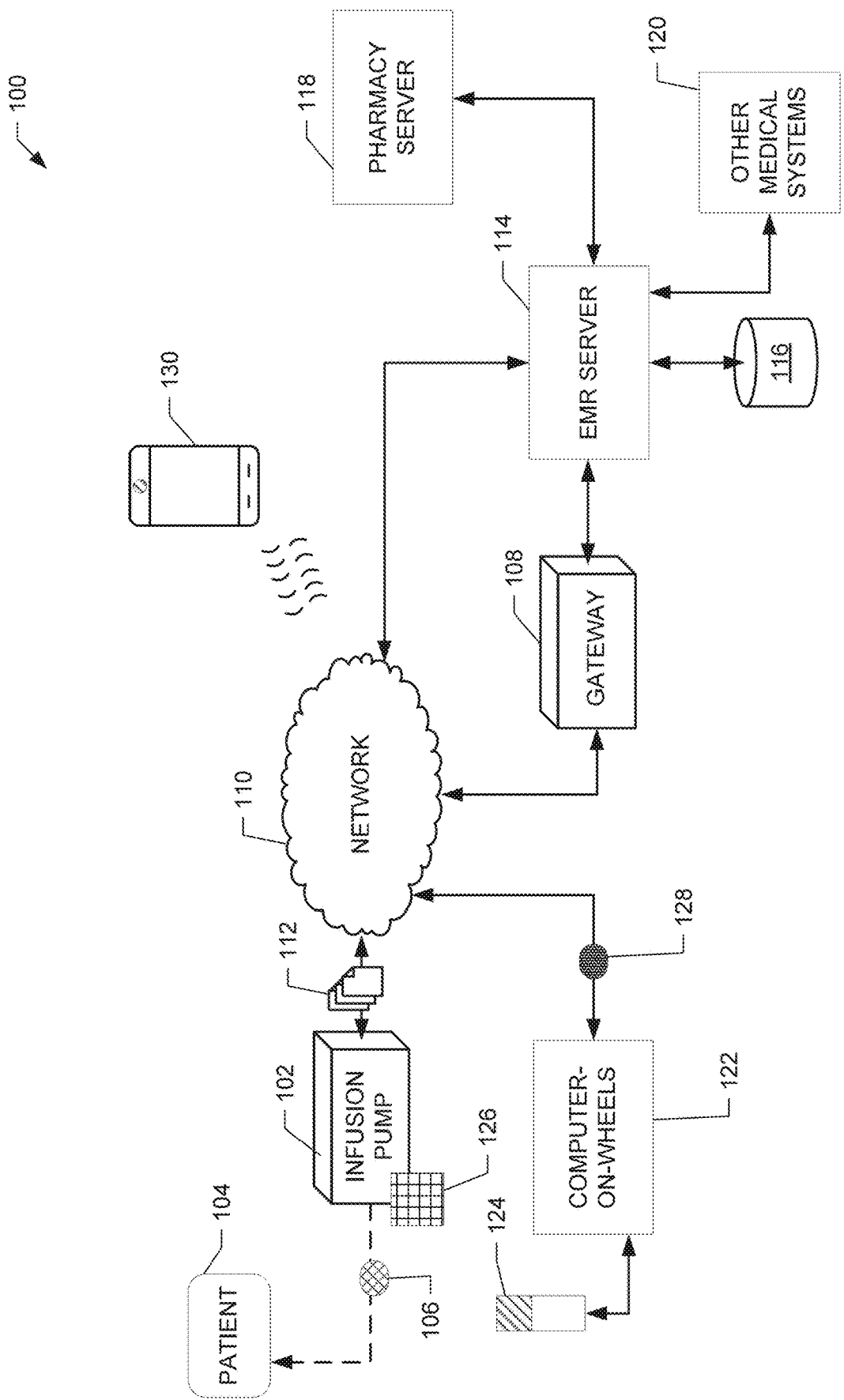
FIG. 1 shows a diagram of a medical environment configured for the example methods, apparatus, and system described herein, according to an example embodiment of the present disclosure.

The present disclosure relates in general to methods, systems, and apparatuses for automatically providing medical record documentation (i.e., auto-document) by back-associating medical device data with a patient's electronic medical record ("EMR"). The back-association of medical data enables a clinician to associate a medical device with a patient's EMR while a medical device is administering a treatment. The back-association may also occur after the medical device has completed a treatment. The disclosed system, apparatuses, and methods automatically write medical device data to a patient's EMR after a back-association has occurred, thereby relieving a clinician from having to manually locate and copy medical device data to a patient's EMR.

In known medical systems, if an association between a patient's EMR and medical device does not occur before a treatment starts, the system stores received data to a temporary or unassociated record in a database. In some instances, known medical systems may even discard medical device data if there is no association with a patient or medication order. After the treatment is complete, a clinician manually copies the medical device data, if it is stored, from the temporary or unassociated record in the database to the patient's EMR. In some instances, a clinician may forget to copy the medical device data to the patient's EMR, thereby leaving an incomplete medical record. In other instances, a clinician may copy the wrong medical device data or only a portion of the medical device data to the patient's EMR.

As disclosed herein, the example methods, systems, and apparatuses enable association between medical device data regardless of a state of a medical treatment. In an example embodiment, a clinician manually programs a medical device to provide a therapy to a patient. The manual programming of the medical device leaves the medical device unassociated with the patient's EMR because there is no correlation between an identifier of the medical device and a patient identifier or medication identifier located in the patient's EMR. As such, when the treatment is started, the medical device is not associated with the patient from the perspective of an EMR server, which receives the data from the medical device. The EMR server is configured to store the medical device data to a temporary location or unassociated record that is indexed, for example, by an identifier of the medical device (which is included within the data).

To enable association after a treatment has begun, the medical device provides or displays an identifying code. The identifying code (e.g., an identifier) may include a code printed on a label attached to the medical device or an electronic code displayed on a screen of the device. While the medical device is providing a treatment to a patient (or after a treatment has been copleted), the clinician scans or otherwise causes an electronic scanning device to obtain electronic information of the identifying code of the medical device. The clinician may also scan an identifying code of the patient (as provided on a patient wristband, for example) and/or an identifying code of a medication container (which corresponds to a medication identifier). The scanned medical device identifier and the patient and/or medication container identifier are transmitted to the EMR server. After receiving the scanned information, the EMR server is configured to associate the medical device with the patient's EMR and/or the medication order. In some examples, the EMR server is configured to update an association table, record, or index such that the medical device data received from the medical device is stored to an EMR of the patient, instead of being discarded or stored to the temporary/unassociated record. In some embodiments, the EMR server is configured to access the previously stored unassociated medical information or device data from the medical device (corresponding to the same treatment session) for copying or otherwise moving this data to the patient's EMR. Accordingly, the example methods, systems, and apparatuses disclosed herein enable a clinician to automatically back-associate medical device data with a particular patient and/or medication order by scanning or otherwise obtaining a medical device identifier after a treatment has already began (or finished) on the medical device.

The example method, system, and apparatus may operate in connection with one or more medical devices. As disclosed herein, a medical device may include an infusion pump, a renal failure therapy device, a patient bedside monitor, a physiological sensor, blood pressure cuff, weight scale, etc. Each medical device is assigned or provided a unique identifier. As disclosed herein, the identifier may include a physical and/or electronic code that is indicative of device identification information. The device identifier may include, for example, alpha-numeric characters. The device identifier may also include a coding of characters in a barcode, quick-response ("QR") code, a near-field communication ("NFC") microchip, a radio-frequency identification ("RFID") microchip, etc.

The medical devices are configured to generate and transmit medical device data. As disclosed herein, medical device data includes device operating parameters, treatment/therapy progress, alarms/alerts, events, diagnostic information, etc. For an infusion pump medical device, the device data may include an infusion rate, a dose, a total volume infused, a time remaining for the therapy, a medication concentration, rate change, a volume remaining within a medication container, a medication name, a patient identifier, titration information, bolus information, a care area identifier, a timestamp when the data was generated, an alarm condition, an alert condition, an event, etc.

As disclosed herein, the example systems, methods, and/or apparatuses are configured to associate a medical device with a patient's EMR in a database to enable medical device data to be written or otherwise stored to the patient's EMR. In some instances, the example systems, methods, and/or apparatuses may associate a medical device to a patient's medication order in a database. In these instances, the medical device data is written or stored to the medication order. It should be appreciated that references herein to a patient's EMR may be interchanged with a medication order.

Medical Environment Embodiment

FIG. 1 shows a diagram of a medical environment 100 configured for the example methods, apparatuses, and systems described herein, according to an example embodiment of the present disclosure. The example environment 100 includes one or more medical device such as, for example, an infusion pump 102. It should be appreciated that the example hospital environment 100 may include other types of medical devices and/or a plurality of pumps 102, renal failure therapy machines, patient monitors, and/or sensors. In the illustrated example, the infusion pump 102 is configured to provide an infusion therapy to a patient 104 by infusing (via an IV line set) one or more fluids 106 (e.g., a medication or a drug).

The example infusion pump 102 may include any pump capable of delivering an intravenous therapy to the patient 104 via one or more line sets. Examples include a syringe pump, a linear peristaltic pump, a large volume pump ("LVP"), an ambulatory pump, multi-channel pump, etc. A syringe pump uses a motor connected to a drive arm to actuate a plunger within a syringe. A linear peristaltic pump uses a rotor to compress part of a tube while rotating. Oftentimes, one or more rollers of the rotor contact the tube for half a rotation. The compressed rotation causes a defined amount of fluid to pass through the tube. LVPs typically use one or more fingers or arms to compress a portion of intravenous therapy ("IV") tube. The timing of the finger actuation on the tube causes constant or near constant movement of a fluid through the tube.

Figure 2:
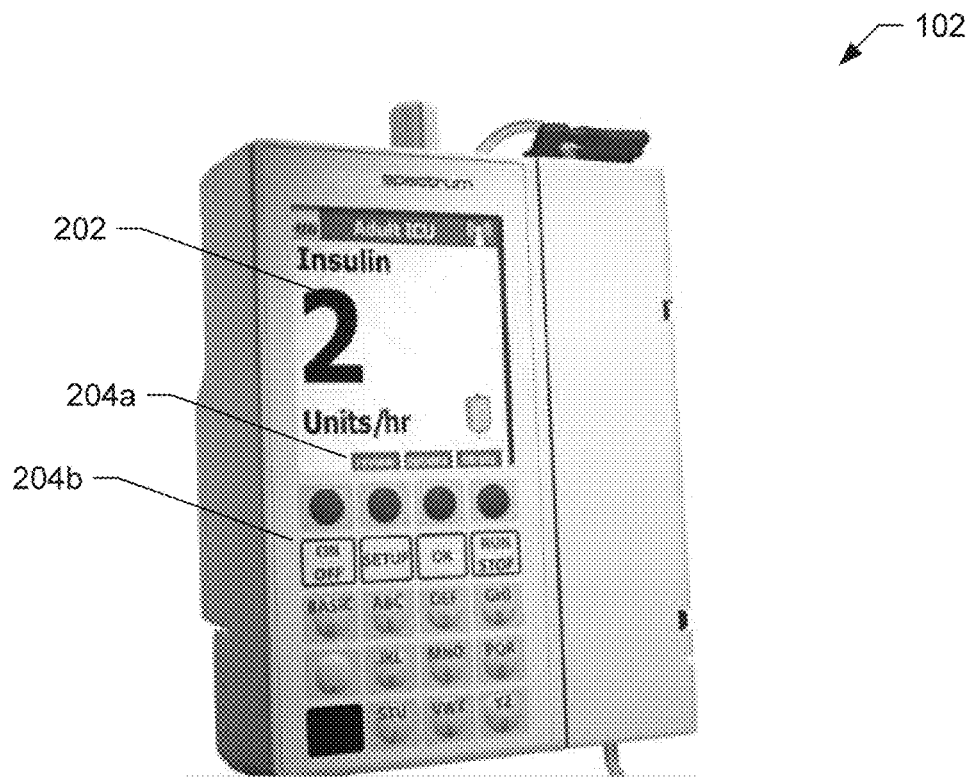
FIG. 2 shows a diagram of an example infusion pump comprising the Baxter® SIGMA Spectrum pump, which may be included within the hospital environment of FIG. 1, according to an example embodiment of the present disclosure.

FIG. 2 shows a diagram of an example infusion pump 102, according to an example embodiment of the present disclosure. The illustrated infusion pump 102 is the Baxter® SIGMA Spectrum™ pump. The illustrated infusion pump 102 includes a display 202 with interfaces 204a and 204b to enable a clinician to specify or program an infusion therapy. As disclosed herein, at least one of the interfaces 204a and 204b are configured to cause the infusion pump 102 to display a device identifier code on the display 202 when actuated.

Other examples of infusion pumps that may be included in the medical environment 100 of FIG. 1 include a linear volume parenteral pump described in U.S. Publication No. 2013/0336814, a syringe pump described in U.S. Publication No. 2015/0157791, an ambulatory infusion pump described in U.S. Pat. No. 7,059,840, an infusion pump described in U.S. Pat. No. 5,395,320, and an infusion pump described in U.S. Pat. No. 5,764,034, the entirety of each are incorporated herein by reference.

Returning to FIG. 1, the example infusion pump 102 is communicatively coupled to a gateway 108 via a network 110. The example gateway 108 is configured to receive infusion pump data 112 (e.g., medical device data) from the infusion pump 102, and route the data 112 to an EMR server 114. In some embodiments, the gateway 108 is configured to convert the data from, for example, EXTCOM message(s) to HL7 message(s).

The example gateway 108 may also be configured to transmit operating parameters or a prescription parameters to the infusion pump 102. For example, the gateway 108 may send an electronic prescription (or software update) to the infusion pump 102 at a predetermined time and/or when the infusion pump 102 is available to accept the prescription. In other instances, the infusion pump 102 may be configured to periodically poll the gateway 108 to determine if an electronic prescription (or software update) is awaiting to be downloaded to the pump. The infusion pump 102 may include a memory storing one or more drug libraries that include particular program parameter limits based on care area, dose change, rate of change, drug type, concentration, patient age, patient weight, etc. The limits are configured to ensure that a received prescription or entered infusion therapy is within acceptable ranges and/or limits decided by a medical facility, doctor, or clinician.

The infusion pump 102 is configured to perform an infusion therapy or treatment on the patient 104, which includes infusing one or more solutions 106 or medications into the patient. The infusion pump 102 operates according to an infusion prescription entered by a clinician at a user interface of the pump (e.g., the interface 204 of FIG. 2) or received via the infusion gateway 108. The infusion pump 102 may compare the prescription to the drug library and provide any alerts or alarms if a parameter of the prescription violates a soft or hard limit. The infusion pump 102 is configured to monitor the progress of the therapy and periodically transmit infusion therapy progress data 112 (e.g., medical device data) to the gateway 108. The therapy progress data 112, as disclosed herein, may include, for example, an infusion rate, a dose, a total volume infused, a time remaining for the therapy, a medication concentration, rate change, a volume remaining within a medication container, a medication name, a patient identifier, titration information, bolus information, a care area identifier, a timestamp when the data was generated, an alarm condition, an alert condition, an event, etc. The infusion pump 102 may transmit the data continuously, periodically (e.g., every 30 seconds, 1 minute, etc.), or upon request by the gateway 108.

The infusion gateway 108 of FIG. 1 includes a server, processor, computer, etc. configured to communicate with the infusion pump 102. The infusion gateway 108 may include, for example, the Baxter® CareEverywhere gateway. In some embodiments, the gateway 108 may be communicatively coupled to more than one infusion pump. The infusion gateway 108 is configured to provide bi-directional communication with the pump 102 for the wired/wireless secure transfer of drug libraries, infusion prescriptions, and therapy progress data 112. The gateway 108 may also be configured to integrate with the EMR server 114 or other hospital system to facilitate the transmission of the infusion therapy progress data 112 from the pump 102 to, for example, a hospital electronic medical record ("EMR") related to the patient 104.

The example EMR server 114 is communicatively coupled to an EMR database 116 for storing EMR records. The EMR database 116 may also be configured to store infusion pump data 112 that is not associated to a particular patient and/or medication order. The EMR server 114 is also communicatively coupled to a pharmacy server 118, which is configured to create and/or transmit medication orders corresponding to, for example, a prepared medication 106. A medication order includes an electronic record or entry, which identifies a patient (e.g., a patient identifier) and infusion parameters for administration. The medication order is assigned a unique identifier. In some embodiments, the medication order may be printed on a label attached to a medication container. The medication order itself associates a patient identifier with a medication identifier. The example EMR server 114 is configured to use the patient identifier in the medication order to store or otherwise associate the medication order with a patient's EMR.

While the pharmacy server 118 and EMR database 116 are shown as being connected directly to the EMR server 114, in other examples they may be connected via the network 110. The example network 110 may include any wired or wireless connection (e.g., an Ethernet network, LAN, WLAN, etc.). The example EMR database 116 may be stored in any volatile or non-volatile memory device including RAM, ROM, flash memory, magnetic or optical disks, optical memory, or other storage media. The database 116 may be structured as a relational database or a graph database. If the database 116 includes a graph database, patients, medication orders, medication device data, and identifiers may be provided by separate nodes.

The example environment 100 of FIG. 1 may also include other medical systems 120, such as a hospital information system ("HIS"). An HIS 120 may include one or more servers for analyzing medical data or receiving medical data from other portions of the hospital environment 100. The HIS 120 may include or be communicatively coupled to a laboratory information system, pharmacy system, a policy/procedure management system, or a continuous quality improvement ("CQI") system. The laboratory system is configured to generate medical data based on analysis of patient biological samples. The policy/procedure management system is configured to manage drug libraries and/or thresholds for alarms/alerts. The CQI system is configured to generate statistical and/or analytical reports based on, for example, infusion therapy progress data 112 from one or more patients. The HIS 120 may also include or be connected to one or more monitors configured to display at least a portion of the infusion therapy progress data 112.

The embodiment of FIG. 1 also includes a patient monitor or computer-on-wheels ("COW") 122. The computer or patient monitor 122 is configured to display one or more graphs of physiological data from a physiological sensor and/or medical device data from the infusion pump 102. The monitor may be wired or wirelessly coupled to a sensor, which may include, for example, a heart rate sensor (e.g., an EKG sensor, an ECG sensor), a temperature sensor, a pulse oximetry sensor, a patient weight scale, a glucose sensor, a respiratory sensor, a blood pressure sensor, etc. The computer or patient monitor 122 is configured to display the data from the sensors within a time-based graph. The computer or patient monitor 122 may also display a numerical value of the most recent data from the sensor in addition to color coding the data.

The computer or patient monitor 122 is communicatively coupled to the gateway 108 and/or the EMR server 114. The computer or patient monitor 122 may continuously, periodically, or upon request, transmit the physiological data to the monitor gateway 108 or server 114, which may then write the physiological data to a patient's EMR.

In some embodiments, the monitor 122 includes a COW. The example COW is configured to provide access to a patient's EMR through the EMR server 114. The example COW is also configured to provide for auto-documentation of the medical device data 112 from the infusion pump 102 and/or provide for auto-programming of the infusion pump 102. In some embodiments, the COW 122 includes or is connected to a barcode scanner 124 or other identifier entry device such as an NFC reader, an RFID reader, a keypad, or a touchscreen interface. The example scanner 124 is configured to read a barcode 126 on the infusion pump 102, a barcode on a patient's wristband, and/or a barcode on a medication container. Information from the read barcodes are transmitted in one or more identifier messages 128 via the network 110 from the COW 122 to the EMR server 114, thereby enabling the server 114 to create an association between the infusion pump 102, the patient 104, and the medication order. In some embodiments, the barcode scanner 124 may be connected to the infusion pump 102 rather than to the COW 122.

In some embodiments, the infusion pump 102 may also be communicatively coupled to one or more physiological sensors. For example, the infusion pump 102 may be connected to a pulse oximetry sensor, a blood pressure cuff, an access disconnection device, and/or a weight scale. The infusion pump 102 may be configured to integrate or otherwise include data from the pulse oximetry sensor into the infusion therapy progress data 112 or, alternatively, transmit the pulse oximetry data separately to the gateway 108.

The example environment 100 of FIG. 1 also includes a clinician device 130 (e.g., a smartphone, tablet computer, laptop computer, workstation, etc.) that enables a clinician to view patient data stored at the EMR database 116. The clinician device 130 may include one or more interfaces or applications for reading and/or writing data stored at the database 116. The clinician device 130 is configured to enable a clinician to view, for example, medication orders for a patient, a patient's EMR, and/or medical device data associated with a patient.

In some embodiments, the environment 100 may include a renal failure therapy ("RFT") machine, which may include any hemodialysis, hemofiltration, hemodiafiltration, continuous renal replacement therapy ("CRRT"), or peritoneal dialysis ("PD") machine. The patient 104, undergoing a renal failure therapy, for example, is connected to the RFT machine, where the patient's blood may be pumped through the machine. The blood passes through a dialyzer of the machine, which removes waste, toxins and excess water from the blood. The cleaned blood is returned to the patient. In PD, treatment fluid is delivered to and removed from a patient's peritoneal cavity to remove toxins and excess water.

Figure 3:
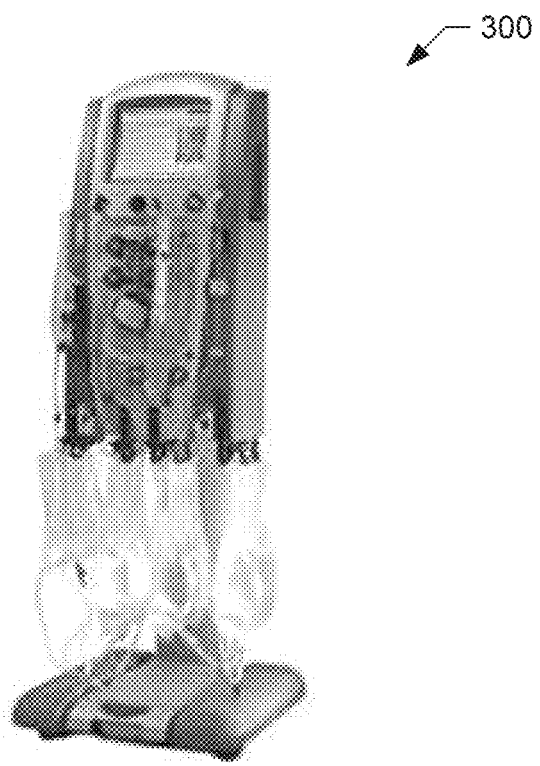
FIG. 3 shows a diagram of an example dialysis or renal failure therapy machine comprising the Gambro® Prismaflex® CRRT machine, which may be included within the hospital environment of FIG. 1, according to an example embodiment of the present disclosure.

FIG. 3 shows a diagram of an example RFT machine 300, according to an example embodiment of the present disclosure. The illustrated RFT machine 300 is the Gambro® Prismaflex® CRRT machine Other examples of RFT machines 300 include a peritoneal dialysis machine described in U.S. Pat. No. 8,403,880, a hemodialysis dialysis machine described in U.S. Publication No. 2014/0112828, and a peritoneal dialysis machine described in U.S. Publication No. 2011/0106002, the entirety of each are incorporated herein by reference.

CRRT is a dialysis modality typically used to treat emergency or critically ill, hospitalized patients in an intensive care unit who develop acute kidney injury ("AKI"). Unlike chronic kidney disease, which occurs slowly over time, AKI often occurs in hospitalized patients and typically occurs over a few hours to a few days.

Hemodialysis is a renal failure treatment in which waste from the blood is diffused across a semi-permeable membrane. During hemodialysis, blood is removed from the patient and flows through a semi-permeable membrane assembly (dialyzer), where the blood flows generally counter-current to dialysis solution flowing on the other side of the semipermeable membrane. In the dialyzer, toxins from the blood travel across the semi-permeable membrane and exit the dialyzer into used dialysis solution (dialysate). The cleaned blood, having flowed through the dialyzer, is then returned to the patient.

In the dialyzer, a pressure differential is created across the semi-permeable membrane by removing dialysate at a flow rate that is greater than that used to introduce the dialysis solution into the dialyzer. This pressure differential pulls fluid containing small, middle, and large molecule toxins across the semi-permeable membrane. Flow and volume measurements are used to control the amount of fluid (ultrafiltration) that is removed. As illustrated above, a hemodialysis machine's pump typically pulls blood from the arterial side of the patient, pushes it into and through the dialyzer, and through a drip chamber that separates out air, before returning the dialyzed blood to the venous side of the patient.

The RFT machine 300 can alternatively be a hemofiltration machine. Hemofiltration is another renal failure treatment, similar to hemodialysis. During hemofiltration, a patient's blood is also passed through a semipermeable membrane (a hemofilter), wherein fluid (including waste products) is pulled across the semipermeable membrane by a pressure differential. This convective flow brings certain sizes of molecular toxins and electrolytes (which are difficult for hemodialysis to clean) across the semipermeable membrane. During hemofiltration, a replacement fluid is added to the blood to replace fluid volume and electrolytes removed from the blood through the hemofilter. Hemofiltration in which replacement fluid is added to the blood prior to the hemofilter is known as pre-dilution hemofiltration. Hemofiltration in which replacement fluid is added to the blood after the hemofilter is known as post-dilution hemofiltration.

The RFT machine 300 can alternatively be a hemodiafiltration machine. Hemodiafiltration is a further renal failure treatment that uses hemodialysis in combination with hemofiltration. Blood is pumped through a dialyzer, which accepts fresh dialysis fluid, unlike a hemofilter. With hemodiafiltration, however, replacement fluid is delivered to the blood circuit, similar to hemofiltration. Hemodiafiltration is accordingly a neighbor of hemodialysis and hemofiltration.

The RFT machine 300 can alternatively be a peritoneal dialysis machine. Peritoneal dialysis uses a dialysis solution, also called dialysate, which is infused into a patient's peritoneal cavity via a catheter. The dialysate contacts the peritoneal membrane of the patient's peritoneal cavity. Waste, toxins and excess water pass from the patient's bloodstream, through the peritoneal membrane and into the dialysate due an osmotic gradient created by the solution. Spent dialysate is drained from the patient, removing waste, toxins and excess water from the patient. This cycle is repeated.

An example peritoneal dialysis machine, operating as the RFT machine 300 of FIG. 3, may perform various types of additional peritoneal dialysis therapies, including continuous cycling peritoneal dialysis ("CCPD"), tidal flow automated peritoneal dialysis ("APD"), and continuous flow peritoneal dialysis ("CFPD"). APD machines perform drain, fill, and dwell cycles automatically, typically while the patient sleeps. APD machines free patients or clinicians from having to manually perform the treatment cycles and from having to transport supplies during the day. APD machines connect fluidly to an implanted catheter, a source or bag of fresh dialysate, and a fluid drain. APD machines pump fresh dialysate from a dialysate source, through the catheter, into the patient's peritoneal cavity. APD machines allow the dialysate to dwell within the cavity, thereby enabling the transfer of waste, toxins and excess water to take place. The source can be multiple sterile dialysate solution bags. APD machines pump spent dialysate from the peritoneal cavity, though the catheter, to the drain. As with the manual process, several drain, fill and dwell cycles occur during APD. A "last fill" occurs at the end of CAPD and APD, which remains in the peritoneal cavity of the patient until the next treatment.

CCPD treatments attempt to drain the patient fully upon each drain. CCPD and/or APD may be batch type systems that send spent dialysis fluid to a drain. Tidal flow systems are modified batch systems. With tidal flow, instead of removing all of the fluid from the patient over a longer period of time, a portion of the fluid is removed and replaced after smaller increments of time.

Peritoneal dialysis dialysate may include a solution or mixture that includes between 0.5% and 10% dextrose (or more generally glucose), preferably between 1.5% and 4.25%. Peritoneal dialysis dialysate may include, for example, Dianeal®, Physioneal®, Nutrineal®, and Extraneal® dialysates marketed by the assignee of the present disclosure. The dialysate may additionally or alternatively include a percentage of icodextrin. It should be appreciated that in some embodiments of the present disclosure, the dialysate may be infused into the patient 110 via the infusion pump 102 rather than the RFT machine 104.

Continuous flow, or CFPD, dialysis systems clean or regenerate spent dialysate instead of discarding it. CFPD systems pump fluid into and out of the patient, through a loop. Dialysate flows into the peritoneal cavity through one catheter lumen and out another catheter lumen. The fluid exiting the patient passes through a reconstitution device that removes waste from the dialysate, e.g., via a urea removal column that employs urease to enzymatically convert urea into ammonia (e.g. ammonium cation). The ammonia is then removed from the dialysate by adsorption prior to reintroduction of the dialysate into the peritoneal cavity. Additional sensors are employed to monitor the removal of ammonia. CFPD systems are typically more complicated than batch systems.

In both hemodialysis and peritoneal dialysis, "sorbent" technology can be used to remove uremic toxins from waste dialysate, re-inject therapeutic agents (such as ions and/or glucose) into the treated fluid, and reuse that fluid to continue the dialysis of the patient. One commonly used sorbent is made from zirconium phosphate, which is used to remove ammonia generated from the hydrolysis of urea. Typically, a large quantity of sorbent is necessary to remove the ammonia generated during dialysis treatments.

Similar to the infusion pump 102, the RFT machine 300 may be programmed locally with a dialysis prescription or receive a dialysis prescription via the gateway 108, or a separate gateway. The RFT machine 300 is configured to perform a renal failure therapy on the patient 104, which, as discussed above, includes removing ultrafiltration from the patient 104. With peritoneal dialysis, the RFT machine 300 infuses dialysate into the patient 104 during the fill cycles. For any dialysis prescription, the RFT machine 300 may compare parameters of the prescription to one or more limits and provide any alerts or alarms if a parameter of the prescription violates a soft or hard limit. The RFT machine 300 is configured to monitor the progress of the therapy and periodically transmit renal failure therapy progress data to the gateway 108. The renal failure therapy progress data may include, for example, a fill rate, a dwell time, a drain or fluid removal rate, a blood flow rate, effluent dose, an ultrafiltration removal rate, a dialysate removal rate, a total dialysate infused, dialysate flow, replacement pre-flow, replacement post-flow, patient weight balance, return pressure, excess patient fluid sign, filtration fraction, a time remaining, dialysate concentration, dialysate name, a patient identifier, a room identifier, a care area identifier, a timestamp when the data was generated, an alarm condition, an alert condition, an event, etc. The RFT machine 300 may transmit the data continuously, periodically (e.g., every 30 seconds, 1 minutes, etc.), or upon request by the gateway 108.

The gateway 108 includes a server, processor, computer, etc. configured to communicate with the RFT machine 300. The gateway 108 may include, for example, the Global Baxter Exchange™ ("GBX") server or gateway. The gateway 108 may be communicatively coupled to more than one RFT machine. The gateway 108 is configured to provide bi-directional communication with the machine 300 for the wired/wireless secure transfer of drug libraries, dialysis prescriptions, and renal failure therapy progress data.

In some examples, the gateway 108 and/or the EMR server 114 include a memory storing machine-readable code or instructions, that when executed by a processor, cause the gateway 108 and/or the EMR server 114 to perform the operations described herein. This includes operating according to a predefined application, routine, or algorithm. The operations include storing un-associated pump data 112 to a temporary location or discarding, associating a patient identifier with a pump identifier in a patient's EMR, and/or triggering the writing of pump data after association to the patient's EMR.

It should be appreciated that the writing of data to a patient's EMR comprises a technical solution to the management of patient data. Unassociated pump data is stored to a first location in the database 116 or memory, which may comprise a temporary memory or association record that is deleted after a predetermined amount of time (e.g., 1 day. 7 days, 30 days, etc.). By comparison, a patient's EMR is stored in the database 116 at a second location or memory that is permanent or semi-permeant. Once a pump-patient association is made, the example EMR server 114 changes a location in the memory or database 116 to where pump data is written. In addition, in some embodiments, the EMR server 114 is configured to move the pump data from the first temporary location to the second more permanent location in the database 116 after an association is made.

Example Association Embodiment

Figure 4:
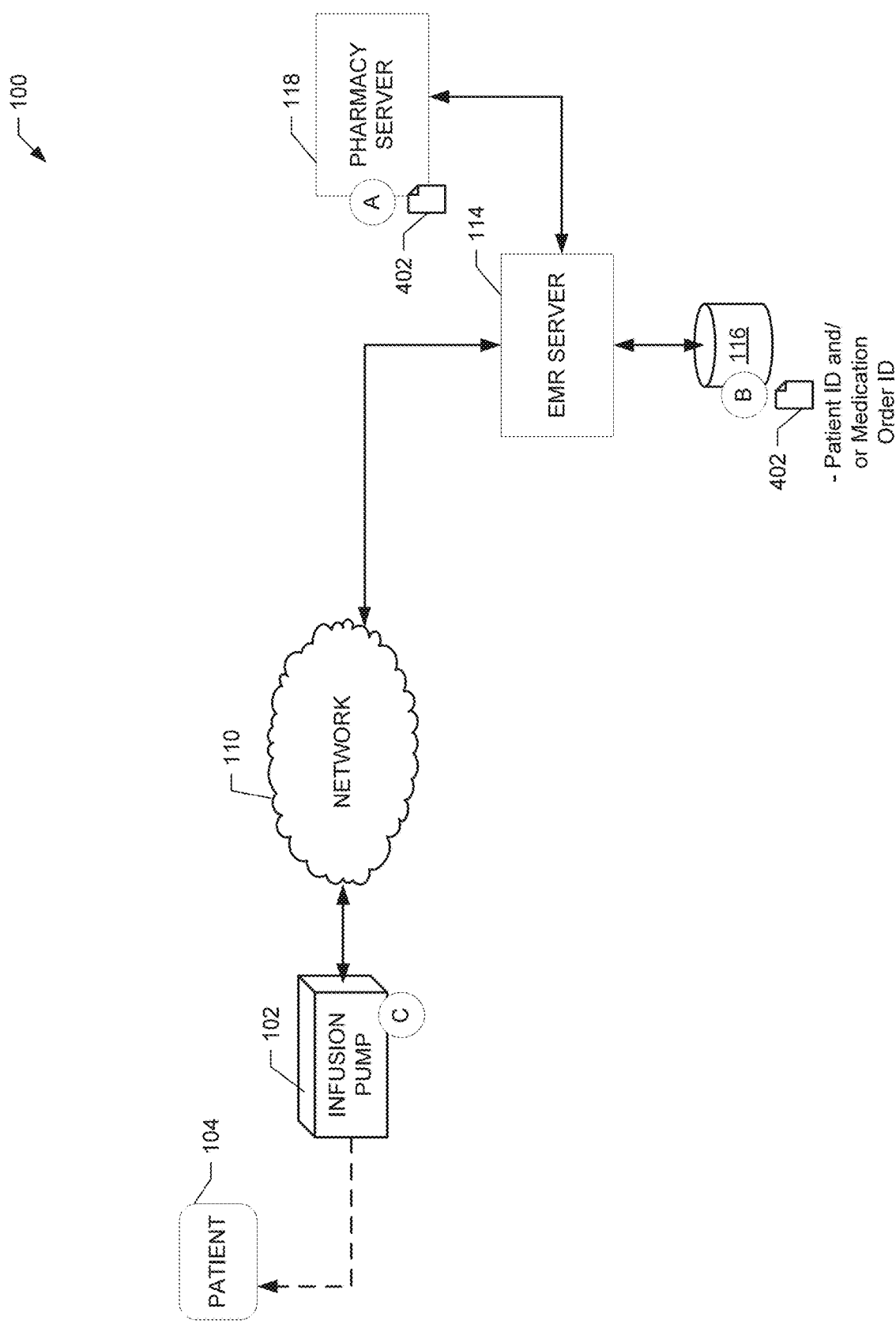
FIGS. 4 to 6 show an example process to back-associate infusion pump data with a particular patient and/or medication order, according to example embodiments of the present disclosure.
Figure 5:
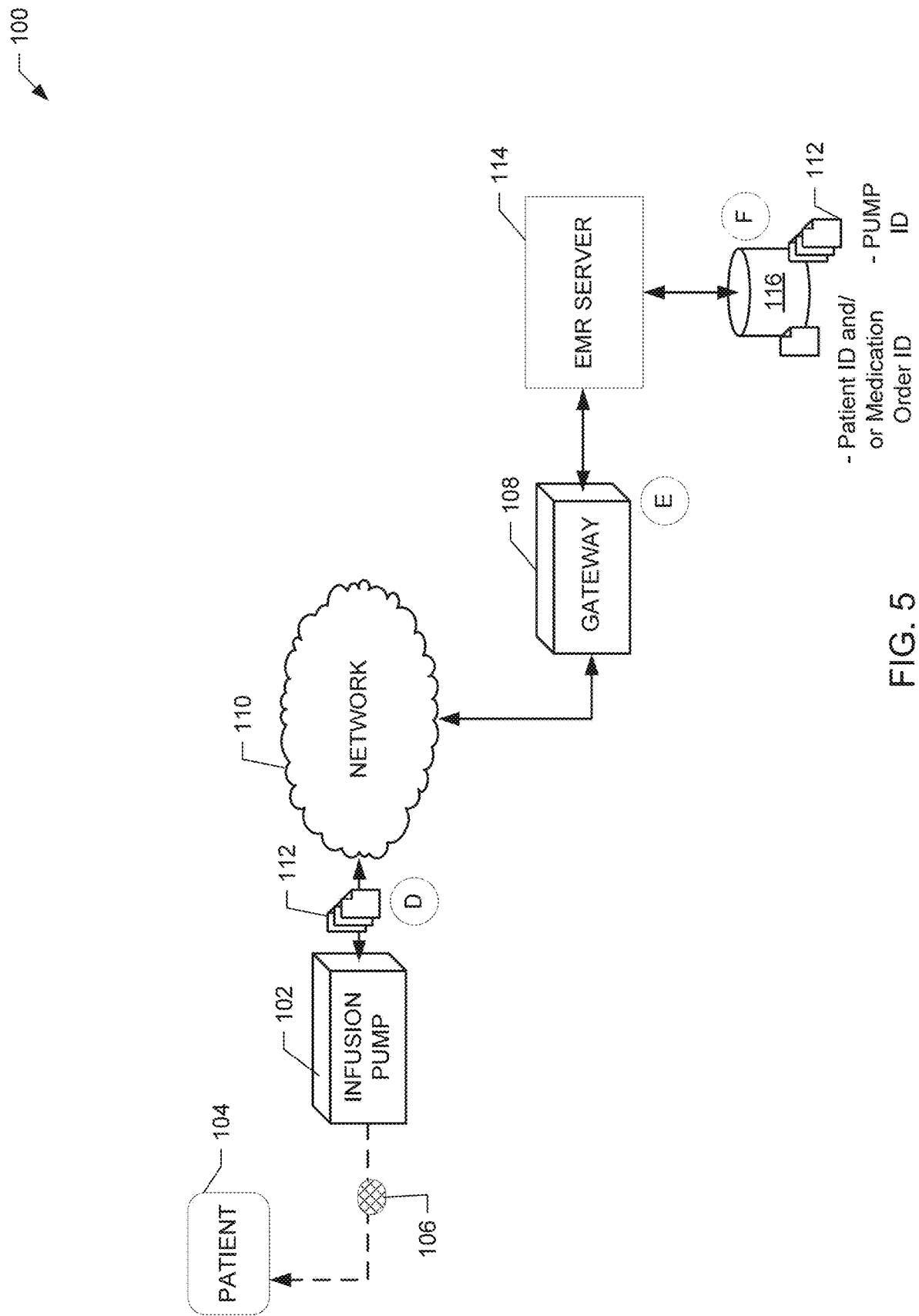
Figure 6:
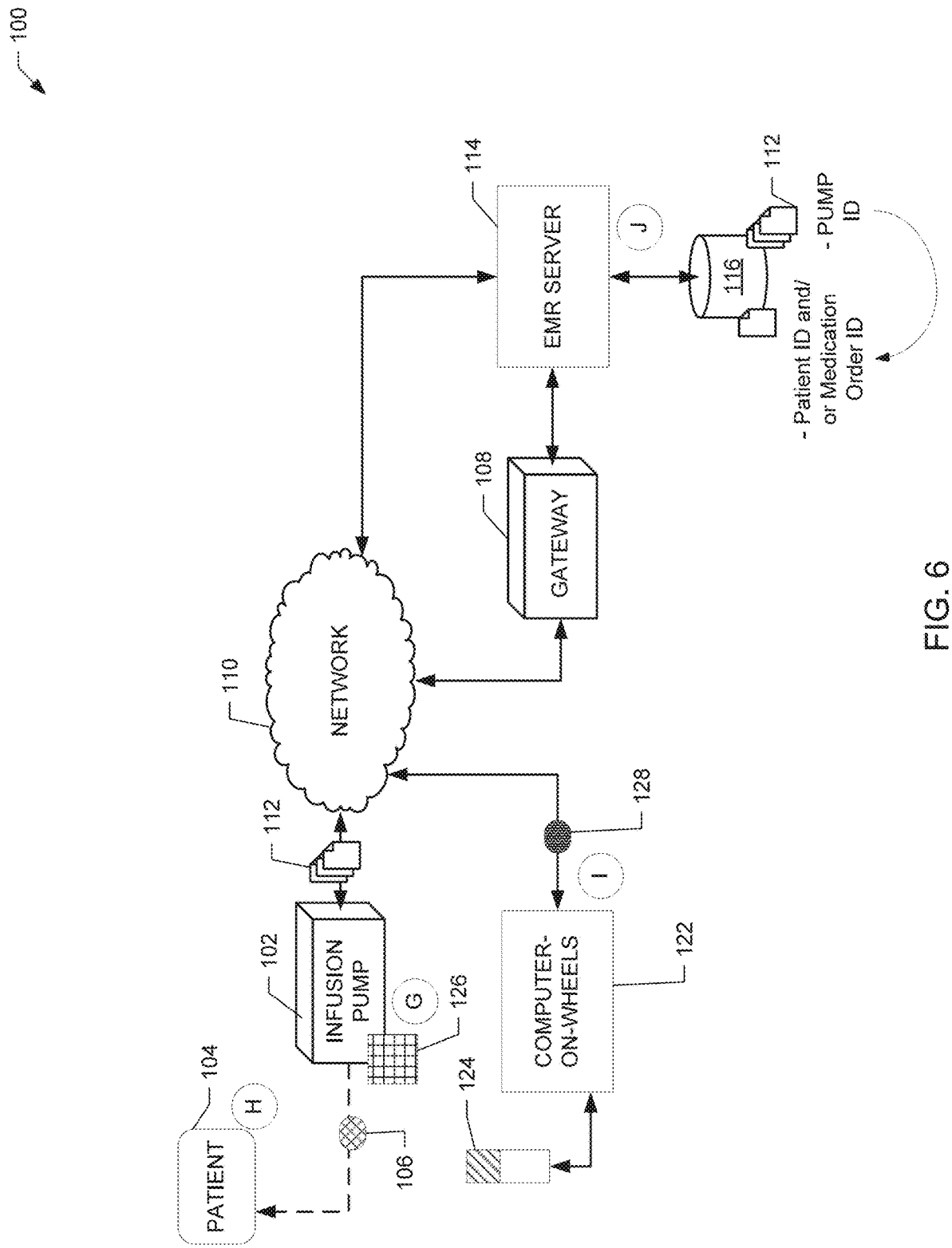

FIGS. 4 to 6 show an example process to back-associate infusion pump data with a particular patient and/or medication order, according to example embodiments of the present disclosure. As described above, back-association enables a clinician to create a correspondence at the EMR server 114 between an infusion therapy that is already in progress (or has already occurred) and a patient's EMR. After a correspondence is made, the EMR server 114 causes subsequent data from the infusion pump 102 to be stored to the patient's EMR or associated medication order. In addition, in some embodiments, the EMR server 114 retrieves or otherwise copies previously un-associated data from the infusion pump (from the same therapy session) for inclusion in the patient's EMR. In other examples, the EMR server 114 does not retrieve the un-associated data.

As shown in FIG. 4, the example process begins when a medication order 402 is created at the pharmacy server 118 (Event A). The medication order 402 includes a patient identifier of the patient 104 that is to receive a medication or fluid that corresponds to the order 402. The medication order 402 may include a name of the fluid, a concentration of the fluid, a dose rate of the fluid, a total volume of the fluid, or any other information for programming the infusion pump 102 to administer the medication. In some instances, at Event A, a label with the medication order information is printed an affixed to a medication container that includes the prepared medication.

At Event B, the EMR server 114 receives the medication order 402 from the pharmacy server 118 and stores the order 402 to the EMR database 116. Using the patient identifier in the order, the EMR server 114 stores the order to an EMR of the patient 104. The medication order may be indexed in the patient's EMR based on the patient identifier and/or the medication order identifier/number.

At Event C, the infusion pump 102 is manually programmed using the medication order parameters. In some embodiments, a clinician manually enters the parameter information into interface(s) 202 and 204 of the infusion pump 102. In other embodiments, a clinician uses a scanner at the pump 102 to read a medication container label of the container with the fluid to be infused. The scanned information includes the infusion parameters, which are automatically populated into appropriate fields in the infusion pump 102. At this point, the infusion pump 102 is ready to begin administering the prescribed medication.

Turning to FIG. 5, the infusion pump 102 begins providing the prescribed fluid 16 to the patient 104. In addition, at Event D, the infusion pump 102 generates therapy progress data 112, which is sent to the gateway 108, via the network 110 (e.g., the pump 102 streams volume, dose and rate infused data). The therapy progress data 112 includes an identifier of the infusion pump 102. At Event E, the gateway 108 receives the data 112 and determines a destination (e.g., the EMR server 114). The gateway 108 may also convert the data 112 from an INTCOM or EXTCOM format into an HL7 format. The converted data 112 is transmitted to the EMR server 114.

At Event F, the EMR server 114 stores the data to the database 116. However, at this point, there is no correspondence between the pump identifier and the patient identifier/order identifier. As a result, the EMR server 114 cannot determine which patient is associated with the data 112. Accordingly, the EMR server 114 is configured to store the data 112 to the database 116 in a separate record (e.g., a temporary record), which may be indexed by the pump identifier.

In FIG. 6, at Event G, a clinician determines, while the therapy is in progress, that the data 112 from the pump 102 needs to be associated with the patient 104 and/or medication order. At this time, the clinician uses the barcode scanner 124 of the COW 122 to scan the pump identifier 126 and a patient identifier and/or medication order identifier. Scanning may include reading a printed code or alphanumeric text, reading an electronic signal provided a RFID/NFC chip, or reading a printed code or alpha-numeric text from an electronic screen.

Figure 7:
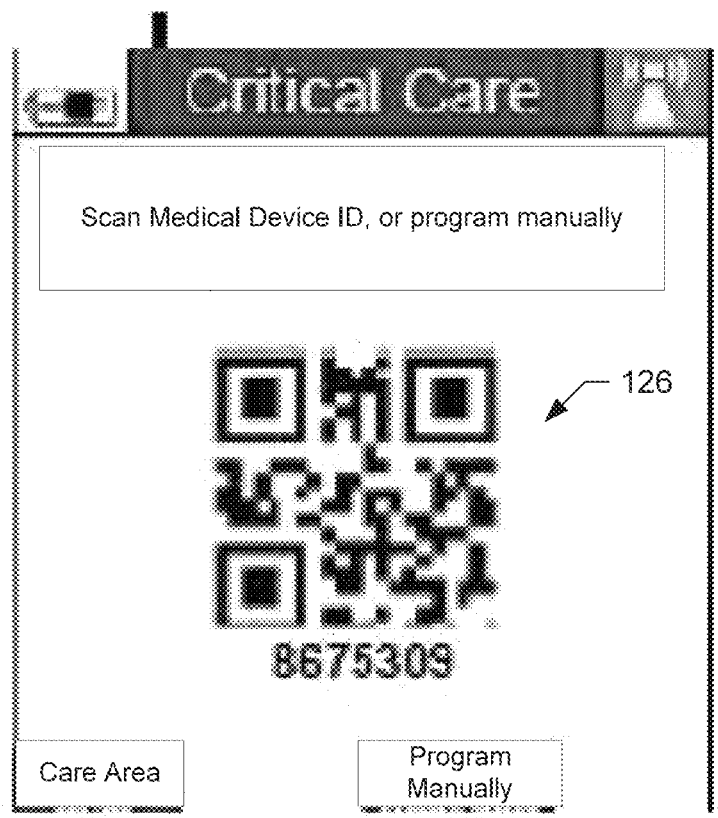
FIG. 7 shows an example QR code as a pump identifier, according to an example embodiment of the present disclosure.

In an example, the clinician actuates a button on the interface 202 or 204 of the infusion pump 102 which causes a QR code to be displayed. FIG. 7 shows an example QR code as the pump identifier 126, according to an example embodiment of the present disclosure. The QR code 126 is displayed on the screen 202 of the infusion pump 102. The clinician uses the barcode scanner 124 to electronically scan the QR code 126 on the screen of the infusion pump. In some embodiments, the code corresponding to the QR code may comprise an encrypted version of the pump identifier, where the gateway 108 and/or the server 114 have a key to decrypt the scanned data to determine the pump identifier.

At Event H, the clinician scans a code associated with the patient 104. The code may be printed on a patient wristband or provided in relation to the patient. The clinician may also scan a code on a medication container. At Event I, the COW 122 sends one or more message 128 that includes information related to the scanned pump identifier 126, the scanned patient identifier, and/or the scanned medication container. The message 128 is transmitted from the COW 122 to the EMR server 114 via the network 110.

At Event J, the EMR server 114 receives the message 128 and determines that the pump identifier corresponds to the patient identifier and/or medication order identifier. The EMR server 114 may store to an entry of an association record, information that is indicative of the association, such as a reference to the pump identifier, the medication order identifier, and/or the patient identifier. The association record may be stored to the database 116. The EMR server 114 may also store the pump identifier to the patient's EMR, which also creates a correspondence between patient identifier, medication order identifier, and pump identifier in the patient's EMR. Thus, subsequent data 112 received from the EMR server 114 from the infusion pump 102 is stored to the patient's EMR. Additionally, in some embodiments, the EMR server 114 copies the previously stored data 112 from the infusion pump for inclusion in the patient's EMR. Once back-associated, the EMR server 114 is able to match previously received and future (for active programs) infusion data (volume, dose, rate) 112 with the correct medication order and place it in the correct patient's EMR.

In some embodiments, the EMR server 114 may prompt a clinician, via the device 130 to verify the auto-documentation data 122 before it is committed to the patient's EMR. The server 114 permits the device 130 to edit the data 112 before, during and after the import. The server 114 may also be configured to enable a clinician, via device 130 to define one or more time window(s) of data that is imported via back-association, so if there is a time period of manual documentation that clinicians do not want to overwrite, they are able to define that.

In some embodiments, the EMR server 114 is configured to provide associations between identifiers for only certain periods of times. For example, an association may only be provided for a duration of a medication order. During a therapy, an infusion pump 102 may provide a therapy identifier or sequence number to identify the particular therapy. The EMR server 114 is configured, in this embodiment, to match only one infusion therapy identifier with the medication order. Thus, if a pump 102 has been associated with the patient, via back-association, and a new therapy begins (where a new therapy order is generated), the EMR server 114 does not automatically write the infusion data 112 to the patient's EMR. Indeed, a new patient may have been connected to the pump 102 for the therapy. Instead, the pump data is stored in a temporary location. If a new medication order is generated and associated with the same patient, the EMR server 114 stores the order to the patient's EMR. The EMR server 114 may then use the previous association as a basis for associating the current pump data with the new medication order (assuming the patient identifier matches the previous patient identifier). This process may be beneficial where an infusion bag is changed at the infusion pump 102 for an ongoing infusion where new treatment parameters have to be entered for the new bag. In instances, where a pump's settings do not have to be changed, merely a new bag replaces an empty bag, the infusion pump continues to use the same therapy number, which continues to be associated with the medication order (for multiple bags) at the EMR server 114.

In other embodiments, a new back-association process must be performed to associate the pump data related to the new therapy with the new medication order. In these other embodiments, a back-association must be made for each new bag or therapy provided at the infusion pump 102.

Example Back-Association Procedure

Figure 8:
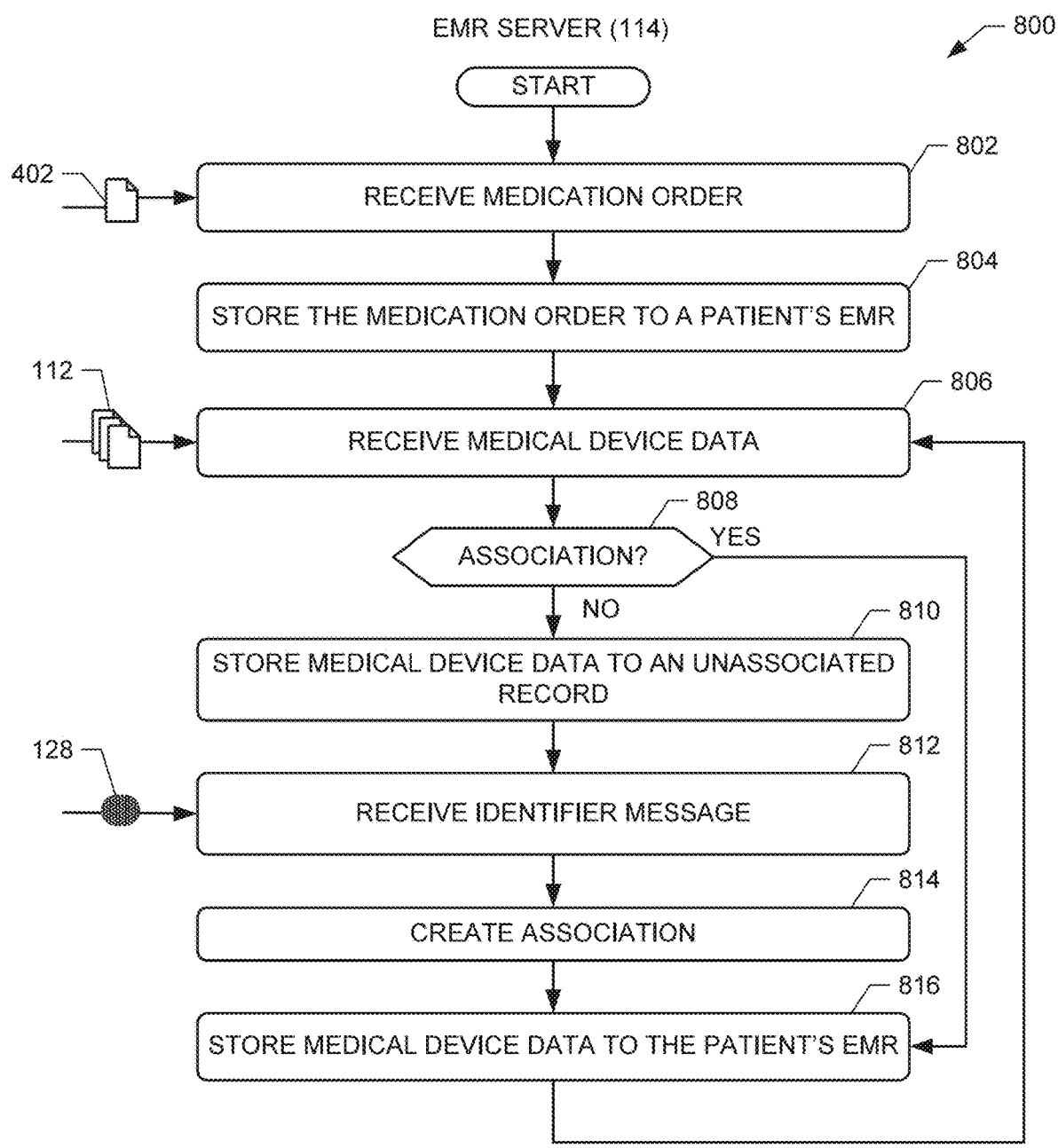
FIG. 8 shows a diagram of an example procedure for associating a medical device with a patient's electronic medical record ("EMR") or medication order, according to an example embodiment of the present disclosure.

FIG. 8 shows a diagram of an example procedure 800 for back-associating medical device data with a patient's EMR or medication order, according to an example embodiment of the present disclosure. Although the procedure 800 is described with reference to the flow diagram illustrated in FIG. 8, it should be appreciated that many other methods of performing the steps associated with the procedure 800 may be used. For example, the order of many of the blocks may be changed, certain blocks may be combined with other blocks, and many of the blocks described are optional. Further, the actions or steps described in procedure 800 may be performed among multiple devices including, for example the EMR server 114, the gateway 108, the medical device 102, the computer 122, and/or the scanner 124.

The illustrated procedure 800 begins when the EMR server 114 receives a medication order 402 from the pharmacy server 118, the HIS 120, and/or the clinician device 130 (block 802). As discussed above, the medication order 802 includes programming or medication parameters related to an administration of a medication, a unique medication identifier, and a patient identifier. The EMR server 114 matches the patient identifier of the medication order 402 to the patient identifier of the patient's EMR in the database 116. The EMR server 114 uses the matching for storing the medication order 402 to the patient's EMR (block 804).

Next, a clinician begins a treatment by programming the medical device 102. As the treatment begins, the medical device 102 transmits medical device data 112 to the EMR server 114 (block 806). The medical device data includes a device identifier of the medical device 102. The EMR server 114 determines if there is an association between the device identifier and any patient identifiers and/or medication order identifiers (block 808). To make the determination, the EMR server 114 may, for example, access an association record of identifier associations and/or read patient EMRs searching for an association.

Figure 9:
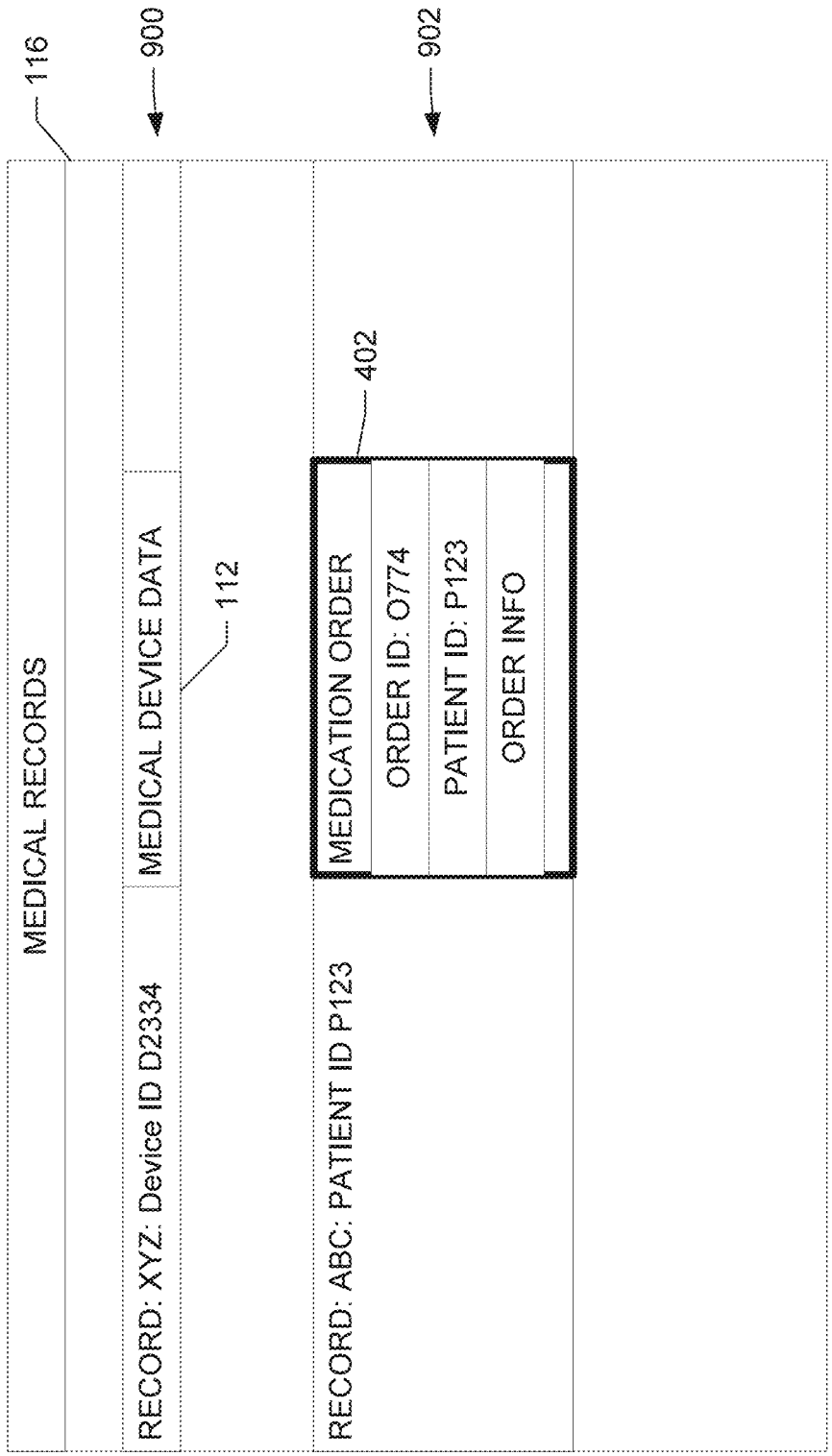
FIG. 9 shows a diagram of a database in which a patient's EMR is unassociated with medical device data from a medical device, according to an example embodiment of the present disclosure.

If there is no association determined, the EMR server 114 stores the medical device data 112 to an unassociated record in the database 116 (block 810). FIG. 9 shows a diagram of the database 116 with the storage of the medical device data 112 to an unassociated record 900, according to an example embodiment of the present disclosure. In the illustrated example, the unassociated record 900 is stored at a first location in the database 116. The record 900 includes the medical device data 112 that is associated with device identifier 'D2334' of the medical device 102. The database 116 of FIG. 9 also includes an EMR 902 of the patient, corresponding to patient identifier 'P123'. The EMR 902 also includes or is associated with the medication order 402, which has an identifier of "O774". The medication order 402 also includes the patient identifier, which the EMR server 114 used for storing the medication order 402 to the patient's EMR 902. As shown, the patient's EMR 902 is located at a second location in the database 902 that is separate from the unassociated record 900.

Returning to FIG. 8, the EMR server 114 receives an identifier message 128 (block 812). The message 128 is received while the treatment is ongoing or after the treatment has ended. The message 128 is generated by, for example, the computer 122 of FIG. 1 in which a connected scanner 128 has scanned a code indicative of an identifier of the medical device 120 and an identifier of the patient and/or an identifier of a medication. To show the device identifier of the medical device 102 for scanning or entry, a clinician may actuate a control on an interface of the medical device 102, causing the medical device 102 to display the device identifier or a graphic (e.g., QR code) that is coded with the identifier.

After receiving the identifier message 812, the EMR server 114 creates an association between the medical device 102 and the EMR of the patient (block 814). To create the association, the EMR server 114 matches the patient or medication order identifier in the message 812 to the corresponding patient or medication order in the patient's EMR. After an association is made, the EMR server 114 stores the association to an association record and/or stores the identifier of the medical device 102 to the medication order 402 and/or the patient's EMR. After the association is created, the EMR server 114 stores medical device data from the medical device 102 to the patient's EMR (block 816). This storage may include storing newly received medical device data and/or medical device data that has already been stored in an unassociated record.

Figure 10:
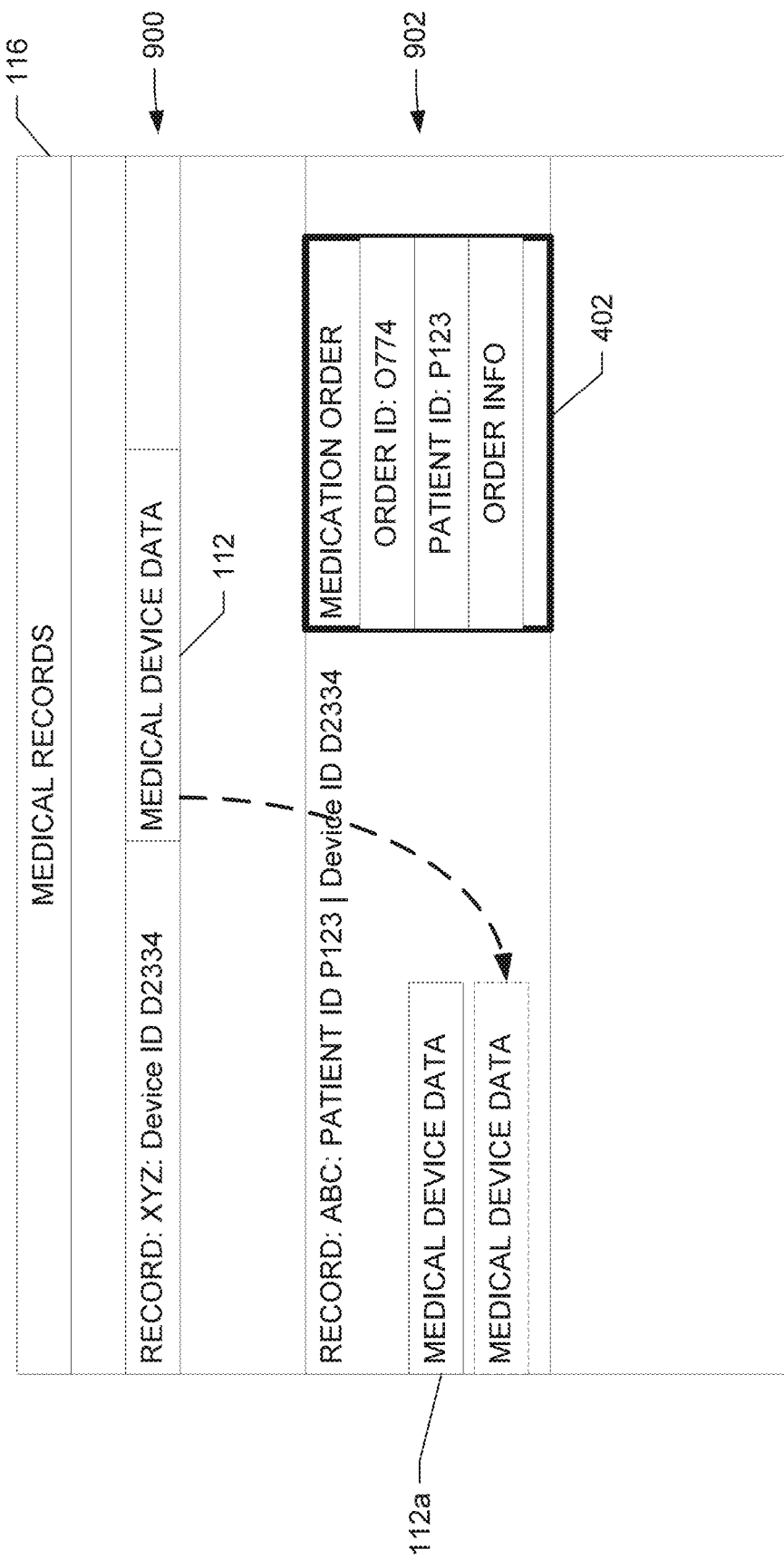
FIG. 10 shows a diagram of the database of FIG. 9 after the patient's EMR is associated with a medical device, according to an example embodiment of the present disclosure.

FIG. 10 shows a diagram of the database 116 of FIG. 9 after the association is made, according to an example embodiment of the present disclosure. As illustrated, the device identifier 'D2334' is added to the EMR 902 of the patient to create the association. New medical device data 112a is stored to the EMR 902. Additionally, in some embodiments, the medical device data 112 at the unassociated record 900 is moved or copied to the patient's EMR 902 by the EMR server 144. The back-association discussed herein accordingly enables medical device data to be stored to the appropriate patient's EMR regardless of when the association was made relative to the start of a treatment.

Auto-Programming Embodiment

Figure 11:
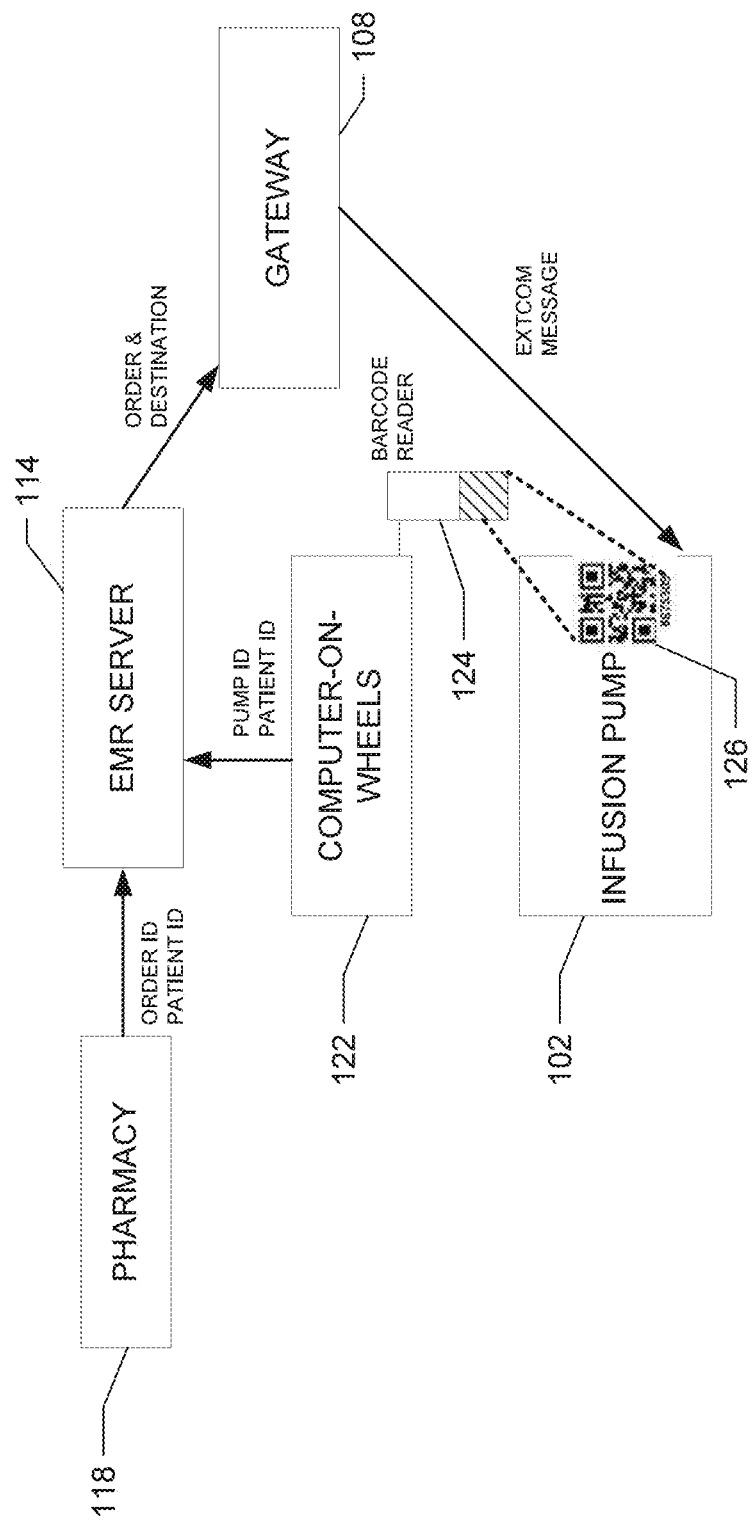
FIG. 11 shows a diagram for auto-programming in the medical environment of FIG. 1, according to an example embodiment of the present disclosure.

FIG. 11 shows a diagram for auto-programming in the medical environment 100 of FIG. 1, according to an example embodiment of the present disclosure. In some embodiments, the pump 102 is configured to be auto-programmed remotely from a pharmacy server 118 or other centralized hospital system. During an infusion therapy set-up, the pump 102 is configured to prompt a clinician to select whether the pump is to be programmed manually or automatically. If manual programming is selected, the pump 102 progresses through a number of screens to enable the clinician to select a drug name, infusion type, volume to be infused and/or infusion rate. In some embodiments, the infusion pump 102 may bypass the manual programming option if the auto-programming feature is enabled. In these embodiments, the infusion pump 102 is configured to display a pump identifier 126 after a care area is selected during a treatment set-up.

For auto-programming, the infusion pump 102 is configured to displays the pump identifier 126 as, for example, a QR code (such as the code shown in FIG. 7). The clinician scans the code with the barcode reader 124 attached to the bedside COW 122. In addition, the clinician scans a patient identifier indicative of the particular patient and/or room and/or a medication container. The COW 122 transmits, via the network 110, a pump identifier (from the QR code) and a patient identifier to the EMR server 114. The identifiers may be included within, for example, an identifier message for the transmission. In addition, the pharmacy server 118 creates an infusion prescription, which directs the preparation of infusion bags having a specified concentration of a drug/medication. The pharmacy server 118 transmits a prescription/medication order to the EMR server 114. The order may specify the volume to be infused, the drug or medication name, the drug concentration, the drug rate, and the patient identifier. The order is transmitted from the pharmacy server 118 to the EMR server 114 using a HL7 protocol message. The HL7 protocol provides a framework specifying how health information is packaged and formatted into messages for seamless integration within a clinician environment.

The EMR server 114 matches the patient identifier received from the COW 122 to the patient identifier within the pharmacy order. After making a match, the EMR server 114 adds the pump identifier to a destination field of the HL7 message, thereby completing the creation of an order for the pump 102. The EMR server 114 transmits the order to the system gateway 108, which is configured with a table of pump identifiers and network IP/MAC addresses of infusion pumps.

The gateway 108 determines an IP/MAC address based on the pump identifier contained within the HL7 message. The gateway 108 also validates the HL7 message, and if successful, converts the message to an EXTCOM message. The gateway 108 then transmits the EXTCOM message through the network 110 to the identified pump 102. To do so, the gateway 108 sends the EXTCOM message to a wireless battery module of the pump 102. The battery module of the pumps 102 waits until its pump processor is available to receive the EXTCOM message. The battery module performs a validation check on the EXTCOM message to ensure its contents have been received successfully. The battery module may further convert the EXTCOM message into an INTCOM message for processing. After the processor in the pump 102 receives the (EXTCOM or INTCOM) message from the battery module, the pump 102 is automatically programed with parameters from the order. The pump 102 compares the parameters to a drug library and displays an alert/warning if any limits are exceeded. Upon receiving confirmation from a clinician regarding the programed parameters, the pump 102 is enabled to provide the prescribed infusion therapy. Data transmitted from the pump 102 is stored by the EMR server 114 to the patient's EMR using the association created when the pump was auto-programmed.

CONCLUSION

It will be appreciated that all of the disclosed methods and procedures described herein can be implemented using one or more computer programs or components. These components may be provided as a series of computer instructions on any conventional computer-readable medium, including RAM, ROM, flash memory, magnetic or optical disks, optical memory, or other storage media. The instructions may be configured to be executed by a processor, which when executing the series of computer instructions performs or facilitates the performance of all or part of the disclosed methods and procedures.

It should be understood that various changes and modifications to the example embodiments described herein will be apparent to those skilled in the art. Such changes and modifications can be made without departing from the spirit and scope of the present subject matter and without diminishing its intended advantages. It is therefore intended that such changes and modifications be covered by the appended claims.

It should be appreciated that 35 U.S.C. 112(f) or pre-AIA 35 U.S.C. 112, paragraph 6 is not intended to be invoked unless the terms "means" or "step" are explicitly recited in the claims. Accordingly, the claims are not meant to be limited to the corresponding structure, material, or actions described in the specification or equivalents thereof.

The invention claimed is:

1. An infusion pump apparatus comprising:
   a drive mechanism configured to move fluid from a fluid container through intravenous tubing to a patient;
   a user interface;
   a display screen;
   a memory device configured to store (i) a device identifier, and (ii) prescription parameters to perform an infusion therapy on a patient; and
   a processor communicatively coupled to the drive mechanism, the user interface, the display screen, and the memory device, the processor configured to:
   cause the drive mechanism to operate according to the prescription parameters to perform the infusion therapy,
   generate first medical device data related to performing the infusion therapy,
   transmit the first medical device data and the device identifier to a server via a network, where there is no association between the device identifier and any patient identifier or medication order such that the server stores the first medical device data to an unassociated record in a database,
   receive a request via the user interface while performing the infusion therapy to display the device identifier,
   cause the device identifier to be displayed on the display screen as a machine-scannable code, where the scanning of the device identifier creates an association, via the server, between an electronic medical record ("EMR") of the patient and the device identifier,
   generate second medical device data related to performing the infusion therapy, and
   transmit the second medical device data and the device identifier to the server via the network, where the association of the EMR and the device identifier causes the second medical device data to be stored to the EMR of the patient.

2. The apparatus of claim 1, wherein the association is created between the EMR of the patient and the device identifier by associating the EMR of the patient with the device identifier, a patient identifier obtained by scanning a code on a patient wrist band, and a medication order that specifies the prescription parameters.

3. The apparatus of claim 2, wherein the association is created between the EMR of the patient and the device identifier by at least one of:
   storing the device identifier and at least one of the patient identifier or a medication order identifier to an entry of an association record;
   storing the device identifier to the EMR of the patient; or
   storing the device identifier to the medication order of the patient.

4. The apparatus of claim 1, wherein the drive mechanism includes at least one of a syringe pump, a linear peristaltic pump, a large volume pump ("LVP"), or an ambulatory pump, or a multi-channel pump.

5. The apparatus of claim 1, wherein the first medical device data and second medical device data include at least one of an infusion rate, a dose, a total volume infused, a time remaining for the infusion therapy, a medication concentration, a rate change, a volume remaining within a medication container, a medication name, a patient identifier, titration information, bolus information, a care area identifier, a timestamp when the first medical device data and second medical device data were generated, an alarm condition, an alert condition, or an event.

6. The apparatus of claim 1, wherein the machine-scannable code includes at least one of alpha-numeric characters, a barcode, or a quick-response ("QR") code.

7. The apparatus of claim 1, wherein the machine-scannable code is configured to be scanned by a bar code scanner that is connected to a computer on wheels.

8. The apparatus of claim 1, wherein the processor is further configured to:
 encrypt the device identifier; and
 cause the device identifier to be displayed on the display screen as an encrypted version of the device identifier.

9. The apparatus of claim 1, wherein the creation of the association between the EMR of the patient and the device identifier causes the first medical device data to be stored to the EMR of the patient.

10. The apparatus of claim 1, wherein the first medical device data and second medical device data are in an INTCOM or EXTCOM format.

11. A medical device data back-association method comprising:
 storing, via a processor of a medical device, prescription parameters;
 causing, via the processor, a drive mechanism to operate according to the prescription parameters to perform a therapy on a patient, the drive mechanism configured to move fluid from a fluid container through tubing to the patient;
 generating, via the processor, first medical device data related to performing the therapy;
 transmitting, via the processor, the first medical device data and a device identifier of the medical device to a server via a network, where there is no association between the device identifier and any patient identifier or medication order such that the server stores the first medical device data to an unassociated record in a database;
 receiving, in the processor via a user interface of the medical device, a request while performing the therapy to display the device identifier;
 causing, via the processor, the device identifier to be displayed on a display screen of the medical device as a machine-scannable code, where the scanning of the device identifier creates an association, via the server, between an electronic medical record ("EMR") of the patient and the device identifier;
 generating, via the processor, second medical device data related to performing the therapy; and
 transmitting, via the processor, the second medical device data and the device identifier to the server via the network, where the association of the EMR and the device identifier causes the second medical device data to be stored to the EMR of the patient.

12. The method of claim 11, wherein the medical device includes at least one of an infusion pump or a renal failure therapy machine.

13. The method of claim 12, wherein the infusion pump includes at least one of a syringe pump, a linear peristaltic pump, a large volume pump ("LVP"), or an ambulatory pump, or a multi-channel pump.

14. The method of claim 11, wherein the association is created between the EMR of the patient and the device identifier by associating the EMR of the patient with the device identifier, a patient identifier obtained by scanning a code on a patient wrist band, and a medication order that specifies the prescription parameters.

15. The method of claim 14, wherein the medication order includes at least one of a medication name, a volume to be infused, a medication concentration, or a medication delivery rate.

16. The method of claim 14, wherein the association is created between the EMR of the patient and the device identifier by at least one of:
 storing the device identifier and at least one of the patient identifier or a medication order identifier to an entry of an association record;
 storing the device identifier to the EMR of the patient; or
 storing the device identifier to the medication order of the patient.

17. The method of claim 11, wherein the first medical device data and second medical device data include at least one of an infusion rate, a dose, a total volume infused, a time remaining for the therapy, a medication concentration, rate change, a volume remaining within a medication container, a medication name, a patient identifier, titration information, bolus information, a care area identifier, a timestamp when the first medical device data and second medical device data were generated, an alarm condition, an alert condition, or an event.

18. The method of claim 11, wherein the machine-scannable code includes at least one of alpha-numeric characters, a barcode, or a quick-response ("QR") code.

19. The method of claim 11, further comprising:
 encrypting, via the processor, the device identifier; and
 causing, via the processor, the device identifier to be displayed on the display screen as an encrypted version of the device identifier.

20. The method of claim 11, wherein the creation of the association between the EMR of the patient and the device identifier causes the first medical device data to be stored to the EMR of the patient.

* * * * *